(12) United States Patent
Chung et al.

(10) Patent No.: US 10,568,828 B2
(45) Date of Patent: Feb. 25, 2020

(54) PEPTIDE HAVING HAIR GROWTH-PROMOTING ACTIVITY AND USE THEREOF

(71) Applicant: CAREGEN CO., LTD., Anyang-si (KR)

(72) Inventors: Yong Ji Chung, Yongin-si (KR); Eun Mi Kim, Yongin-si (KR); Eung-Ji Lee, Anyang-si (KR); Min Woong Kim, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 15/999,744

(22) PCT Filed: Feb. 9, 2017

(86) PCT No.: PCT/KR2017/001409
§ 371 (c)(1),
(2) Date: Aug. 20, 2018

(87) PCT Pub. No.: WO2017/142254
PCT Pub. Date: Aug. 24, 2017

(65) Prior Publication Data
US 2019/0046427 A1  Feb. 14, 2019

(30) Foreign Application Priority Data

Feb. 18, 2016  (KR) ........................ 10-2016-0019292

(51) Int. Cl.
| | | |
|---|---|---|
| A61K 38/08 | (2019.01) | |
| A61K 38/06 | (2006.01) | |
| A61K 38/07 | (2006.01) | |
| A61K 38/00 | (2006.01) | |
| A61P 17/14 | (2006.01) | |
| C07K 5/00 | (2006.01) | |
| C07K 7/00 | (2006.01) | |
| C07K 16/00 | (2006.01) | |
| C07K 17/00 | (2006.01) | |
| A61K 8/64 | (2006.01) | |
| A61Q 7/00 | (2006.01) | |

(52) U.S. Cl.
CPC . A61K 8/64 (2013.01); A61Q 7/00 (2013.01)

(58) Field of Classification Search
None
See application file for complete search history.

(56) References Cited

U.S. PATENT DOCUMENTS

| | | | |
|---|---|---|---|
| 6,696,417 B1 | 2/2004 | Raghupathi et al. | |
| 7,057,013 B1 | 6/2006 | Ezquerro Saenz et al. | |
| 2008/0166757 A1* | 7/2008 | Bron ..................... | C07K 14/32 |
| | | | 435/69.1 |
| 2014/0309157 A1 | 10/2014 | Chung et al. | |
| 2017/0049847 A1 | 2/2017 | Chung et al. | |
| 2019/0119321 A1* | 4/2019 | Chung ................... | A61K 38/08 |

FOREIGN PATENT DOCUMENTS

| | | | | |
|---|---|---|---|---|
| EP | 2740740 A1 | 6/2014 | | |
| EP | 2740741 A1 | 6/2014 | | |
| JP | 2002-501012 A | 1/2002 | | |
| JP | 2005-239695 A | 9/2005 | | |
| KR | 20110032587 A | 3/2011 | | |
| KR | 10-2013-0014700 A | 2/2013 | | |
| KR | 10-2014-0107784 A | 9/2014 | | |
| KR | 10-2015-0130617 A | 11/2015 | | |
| KR | 10-2016-0003610 A | 1/2016 | | |
| KR | 10-2016-0003611 A | 1/2016 | | |
| WO | WO-0206515 A2 * | 1/2002 | ......... | A61K 39/0011 |
| WO | WO-0213799 A2 * | 2/2002 | ......... | C12N 15/1138 |
| WO | WO-2015/174598 A1 | 11/2015 | | |
| WO | WO-2015/174601 A1 | 11/2015 | | |

OTHER PUBLICATIONS

International Search Report dated Jun. 7, 2017 for International Patent Application No. PCT/KR2017/001409, Chung et al., "Peptide Having Hair Growth-Promoting Activity and Use Thereof," filed Feb. 9, 2017 (6 pages).

Extended European Search Report dated Nov. 29, 2018 for European Patent Application No. 17753415.3, Chung et al., "Peptide Having Hair Growth-Promoting Activity and Use Thereof," filed Feb. 9, 2017 (9 pages).

* cited by examiner

*Primary Examiner* — Christina Bradley
*Assistant Examiner* — Zachary J Miknis
(74) *Attorney, Agent, or Firm* — Clark & Elbing LLP; Susan M. Michaud

(57) ABSTRACT

The present invention provides a peptide which shows a hair growth-promoting activity. The peptide of the present invention promotes the growth of follicular cells and increases the expression of a hair growth-related growth factor and hair growth-related factors, thereby showing an excellent effect in hair growth. The peptide of the present invention can be used for preventing and alleviating hair loss, promoting hair growth, and improving hair growth. In addition, the superior activity and stability of the peptide of the present invention allows the peptide to be very favorably applied to quasi drugs and cosmetics.

14 Claims, 18 Drawing Sheets
Specification includes a Sequence Listing.

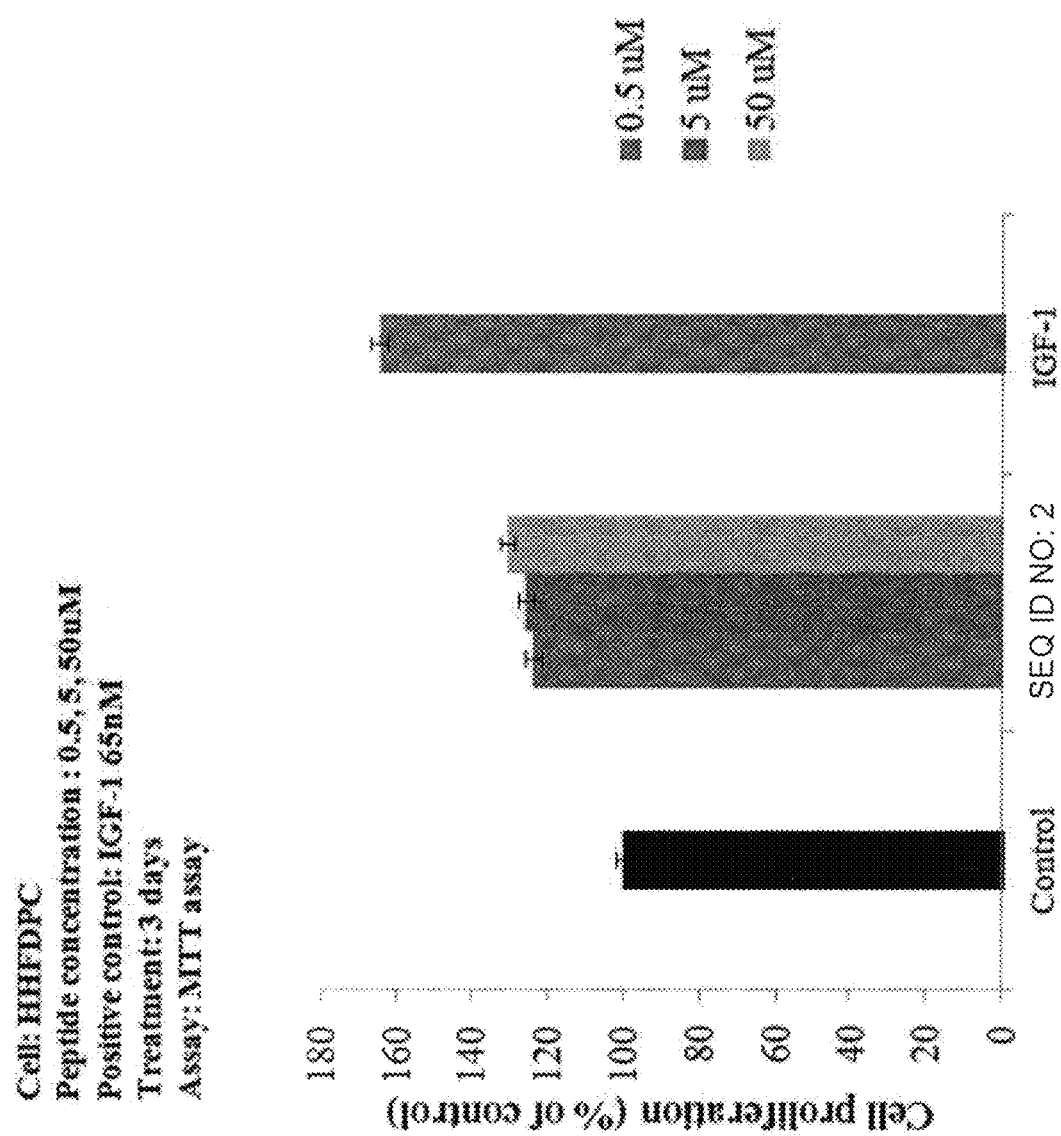

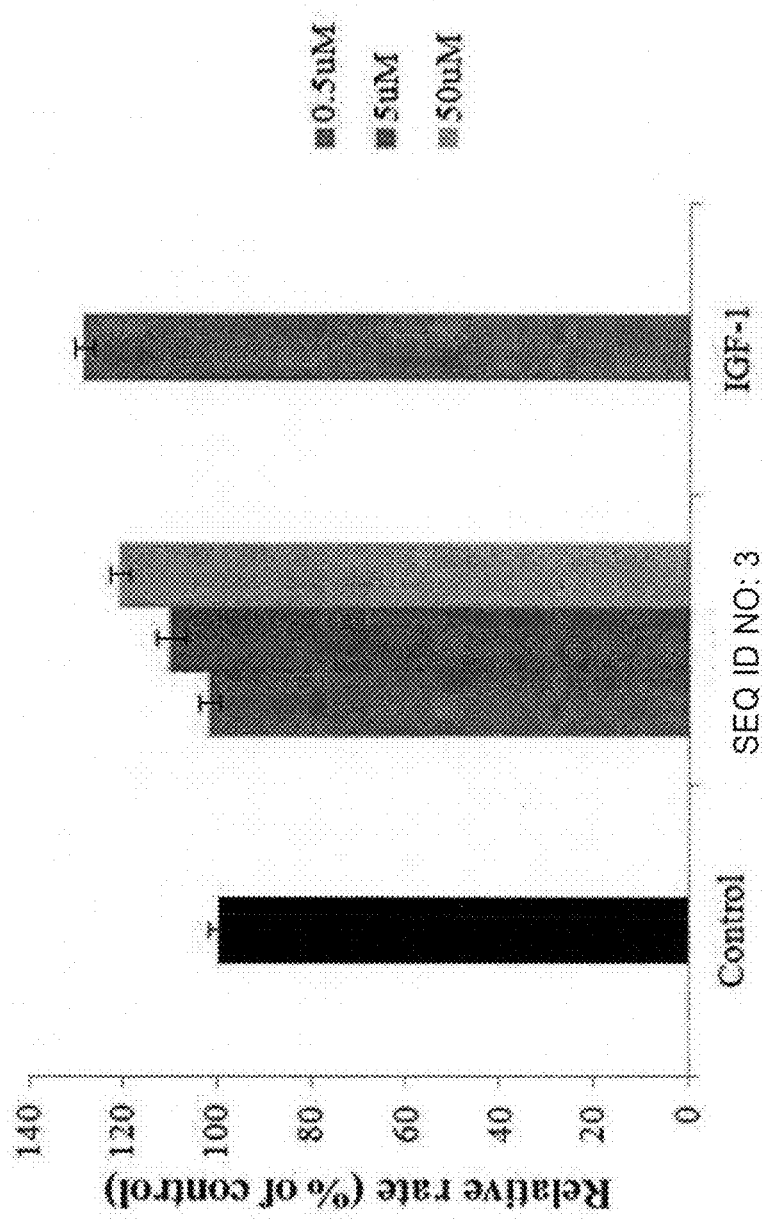

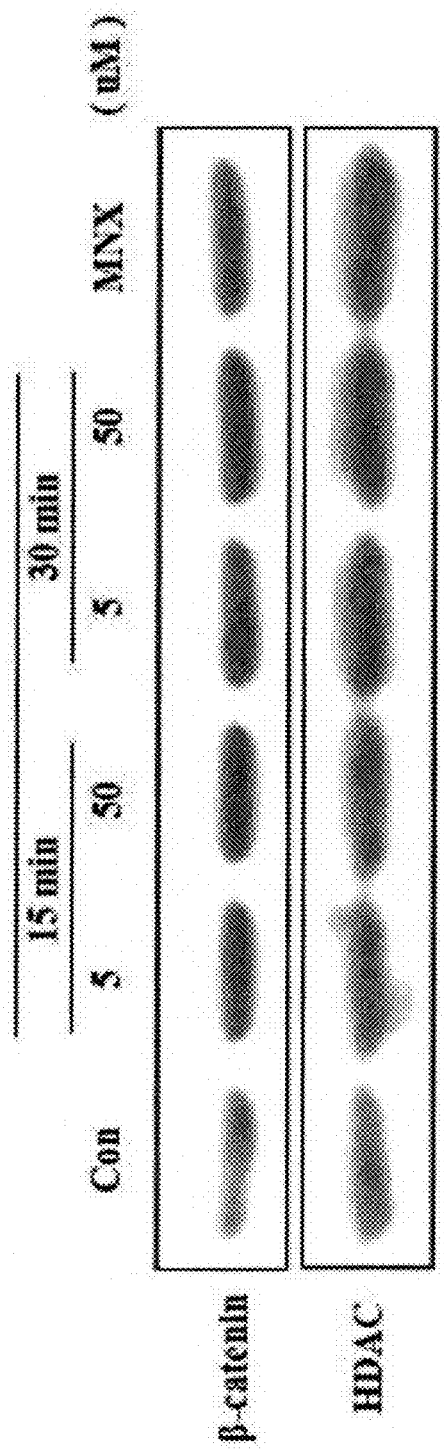

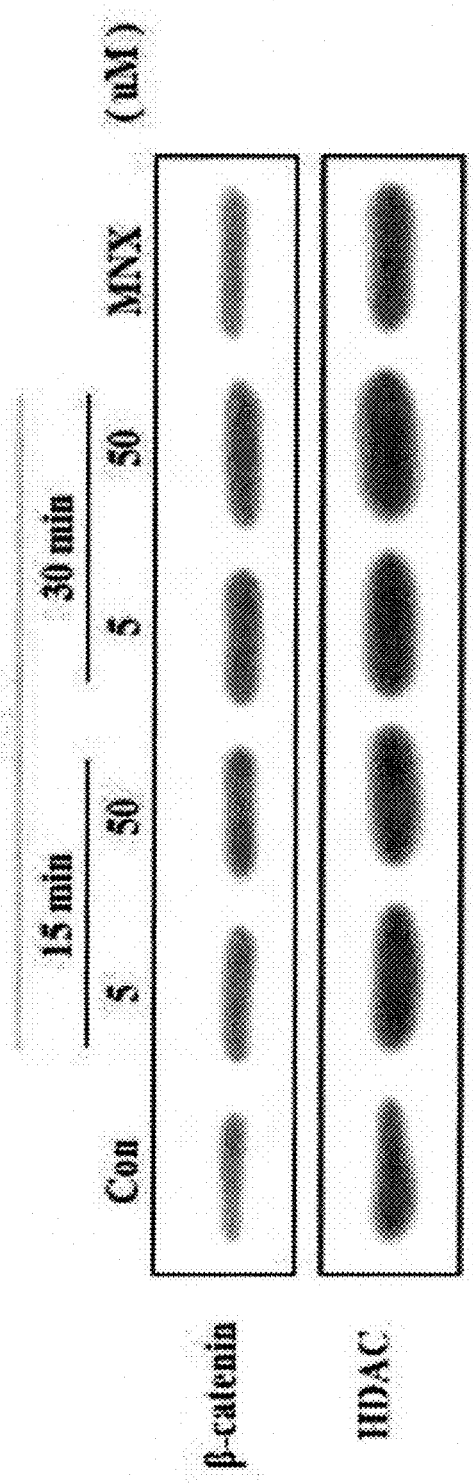

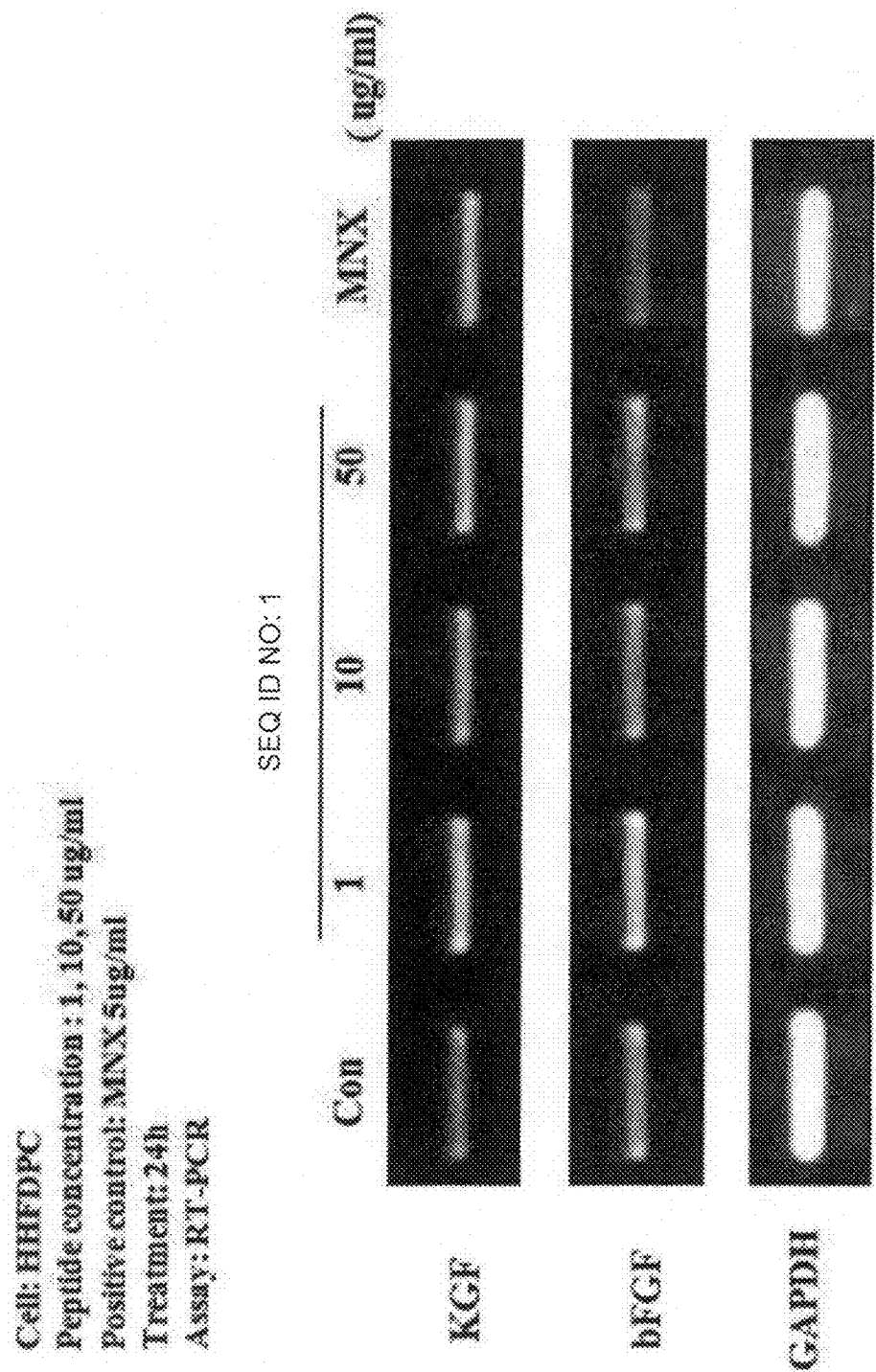

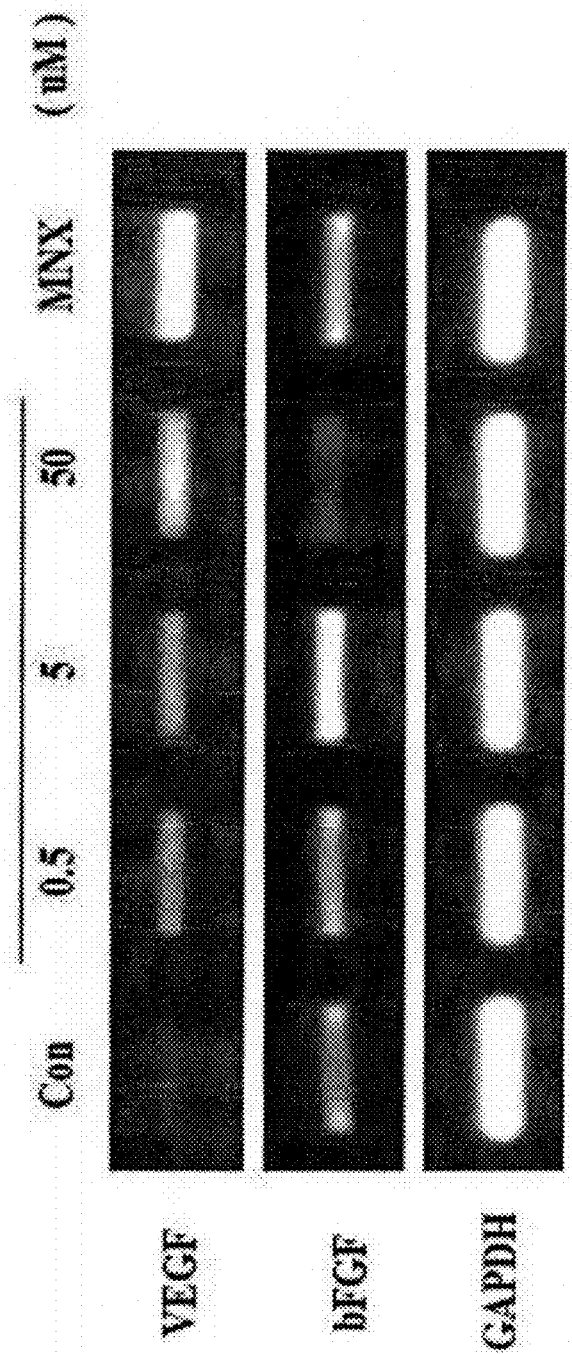

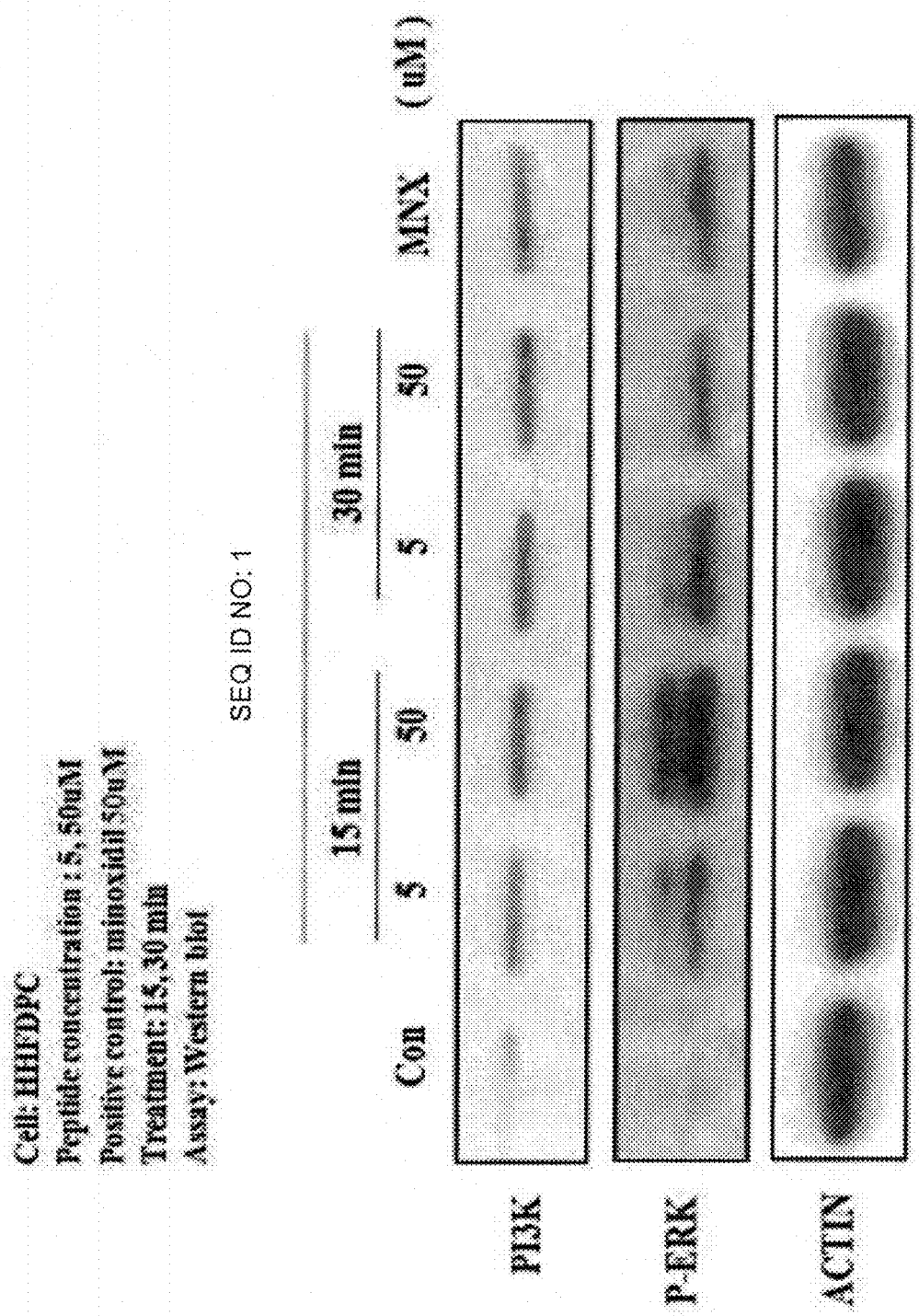

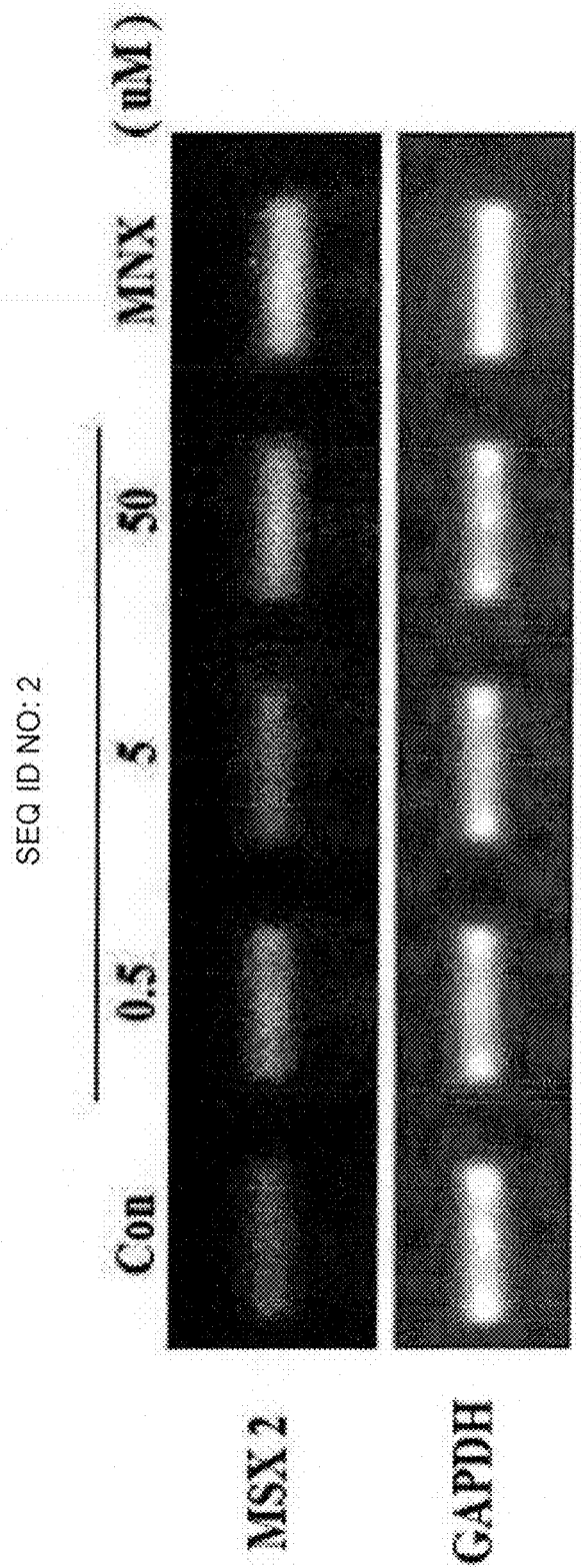

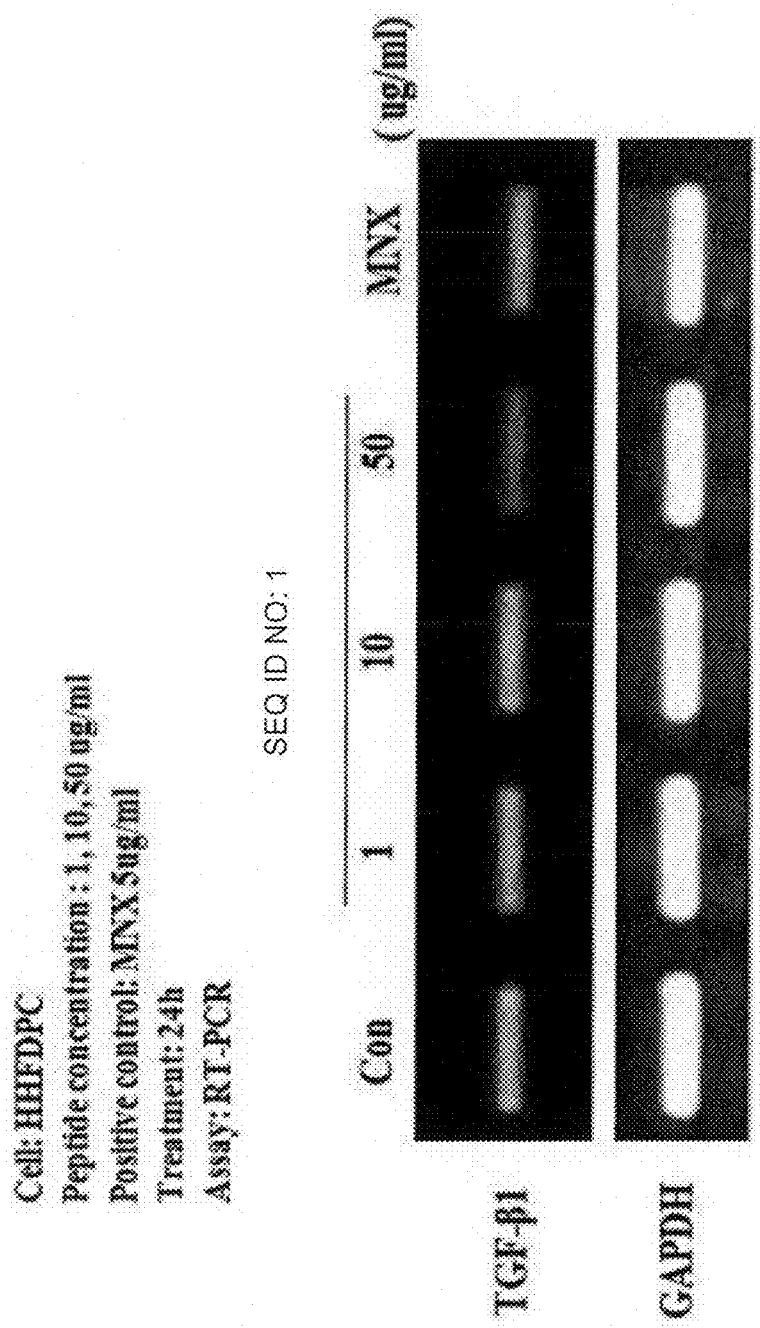

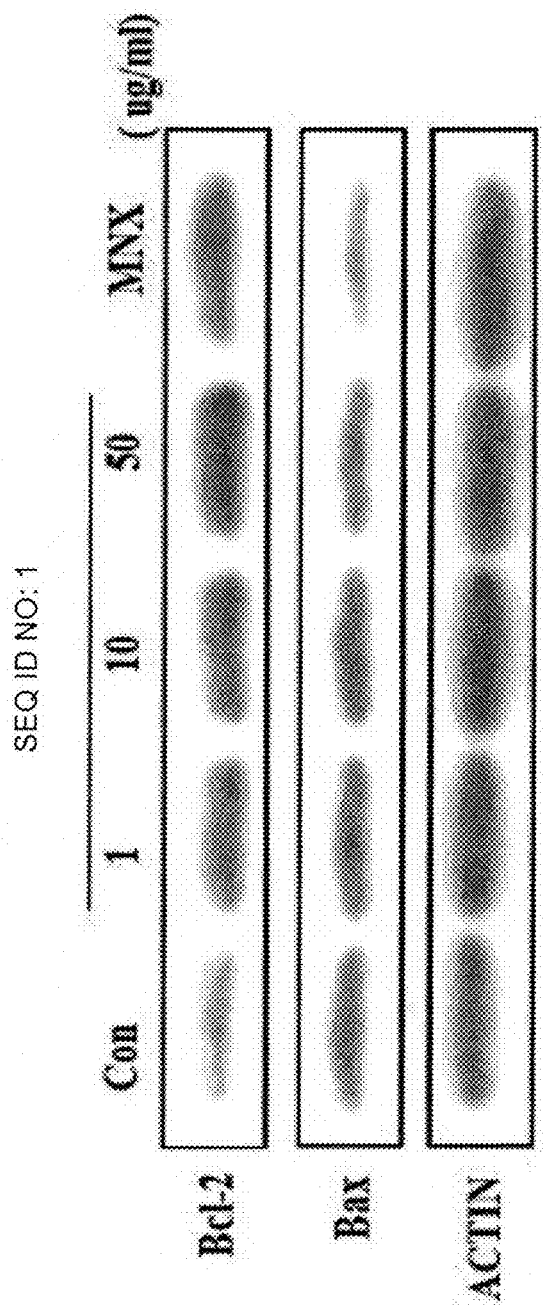

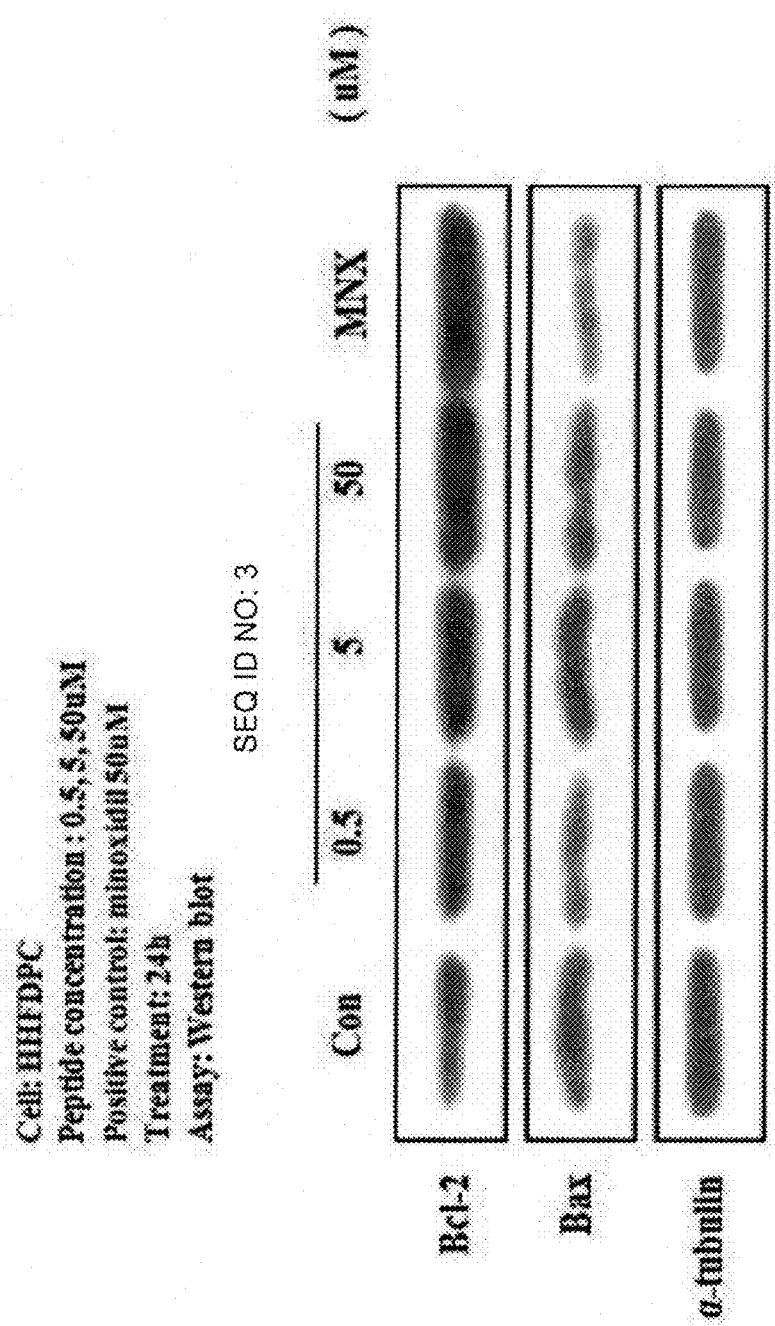

PEPTIDE HAVING HAIR GROWTH-PROMOTING ACTIVITY AND USE THEREOF

TECHNICAL FIELD

The present invention relates to a peptide having an activity to stimulate hair production and/or growth, a composition containing the peptide as an active ingredient for stimulating hair production, and a use of the peptide for stimulating hair production.

BACKGROUND ART

The hair follicle, which is grown from a lower part of the primitive epidermis and extends into a deeper skin layer, is a distinctive organ found in mammalian skin. A cell plug known as a follicle or dermal papilla cell exists in the base of the hair follicle (Stenn and Paus, *Physiol. Rev.*, 81: 449 (2002)), and the papilla is essential in the normal circulation of the hair follicle (Oliver, *Embryol. Exp. Morph.* 15: 3311 (1966); and Oliver, *Embryol. Exp. Morph.* 16: 231 (1966)) and the growth of the hair shaft. The hair shaft is a thread-shaped structure formed of epithelial cells composed of keratin filaments and filament-aggregating proteins tightly attached thereto.

Human hairs fall out and again produce while cyclically repeating anagen, catagen, and telogen phases. The cycle of growth in the hair cycle is determined by regulation of hormones or other growth factors. Severe stress or malnutrition may advance the catagen and telogen phases, leading to severe hair loss (*American Journal of Pathology*, 162(3) (2003), (Arck, Petra Clara; Handjiski, Bori)).

In cases of male-pattern baldness, the hair follicles at the front and top of the scalp are sensitive to androgen. Thus, male-pattern baldness corresponds to the minimization of hair follicles rather than the destruction of hair follicles, and is caused by excessive secretion of the male hormone androgen. The excessive secretion of androgen results in the activation of 5-α reductase, converting testosterone into dihydrotestosterone (DHT). The resulting dihydrotestosterone shortens the cycle of hair growth and miniaturizes hair follicles, decreasing the number of thick strong adult hairs, leading to hair loss.

In general, hair loss increases with aging. For example, different disorder conditions, such as scar conditions associated with cicatricial alopecia, burns or compression injuries, may cause severe hair loss. Several substances as medicaments have been used to treat such a hair loss phenomenon, but the medicaments are expensive or cause several adverse effects.

In addition, these medicaments have drawbacks in that the sustained use thereof is required; hair loss again occurs when the use thereof is stopped; there are individual differences in efficacy; and side effects vary from person to person.

Furthermore, raw materials used as cosmetics have an advantage of being inexpensive, but their efficacy is not great since they contain ingredients derived from plant extracts. Therefore, there is an increasing need in the art for novel effective ingredients that are more economical in terms of costs.

Two available drugs known so far (minoxidil and finasteride) might delay additional hair loss, but do not induce the regeneration of new hair follicles. Among hair cosmetics, a lot of anti-hair loss products using plant extracts and the like have also been released.

For example, the products using plant extracts and the like that have been developed include: products containing extracts of *sophora* root, chili pepper, swertia, *morus* bark, *morus* leaves, *ginseng*, licorice, peony, foxglove, fennel, *cornus* fruit, garlic, and the like; products wherein a composition containing xanthines and growth hormones is added to improve cellular metabolism suppressed by excessive dihydrotestosterone and stimulate hair growth induced by growth hormones, thereby preventing hair loss and attaining hair production, leading to a hair growth stimulating effect; hair production stimulating products that supply nutrients to the scalp and hair through the development of products containing minerals, vitamins, and extracts of green tea, rosemary, mugwort, or licorice, in order to stimulate hair production and hair growth, and have effects in the prevention of hair loss and the stimulation of hair growth; and products for male-pattern baldness wherein the substances, such as vitamin B, vitamin C, vitamin D, vitamin E, nicotinic acid, pantothenic acid, biotin, and folic acid, are mixed with plant extracts to inhibit 5-α reductase, thereby preventing the production of dihydrotestosterone in the metabolism of male hormones and helping hair metabolism. However, products that affect even the production of new hair are difficult to find.

DETAILED DESCRIPTION OF THE INVENTION

Technical Problem

The present inventors endeavored to develop a peptide having excellent hair production and/or hair growth efficacy, and as a result, the present inventors selected three kinds of peptides having excellent efficacy of hair production from peptide libraries of the present inventors and experimentally established the hair production and/or hair growth efficacy thereof, and thus completed the present invention.

Therefore, an aspect of the present invention is to provide a peptide having an activity to stimulate hair production, the peptide consisting of the amino acid sequence selected from the group consisting of SEQ ID NO: 1 to SEQ ID NO: 3.

Another aspect of the present invention is to provide a composition for preventing or improving hair loss, the composition comprising, as an active ingredient, at least one peptide selected from the group consisting of peptides consisting of the amino acid sequence selected from the group consisting of SEQ ID NO: 1 to SEQ ID NO: 3.

Still another aspect of the present invention is to provide a composition for stimulating hair production or hair growth, the composition comprising, as an active ingredient, at least one peptide selected from the group consisting of peptides consisting of the amino acid sequence selected from the group consisting of SEQ ID NO: 1 to SEQ ID NO: 3.

Still another aspect of the present invention is to provide a use of a peptide consisting of the amino acid sequence selected from the group consisting of SEQ ID NO: 1 to SEQ ID NO: 3 for preventing and/or improving hair loss.

Still another aspect of the present invention is to provide a use of a peptide consisting of the amino acid sequence selected from the group consisting of SEQ ID NO: 1 to SEQ ID NO: 3 for stimulating hair production and/or hair growth.

Technical Solution

The present inventors endeavored to develop a peptide having excellent hair production and/or hair growth efficacy, and as a result, the present inventors selected three kinds of peptides having excellent efficacy of hair production from peptide libraries of the present inventors and experimentally established the hair production and/or hair growth efficacy thereof.

In accordance with an aspect of the present invention, there is provided a peptide having an activity to stimulate hair production, the peptide consisting of the amino acid sequence selected from the group consisting of SEQ ID NO: 1 to SEQ ID NO: 3.

The peptide may contain an amino acid sequence selected from the group consisting of SEQ ID NO: 1 to SEQ ID NO: 3, and for example, may be composed of an amino acid sequence selected from SEQ ID NO: 1 to SEQ ID NO: 3.

As used herein, the term "peptide" refers to a linear molecule formed of amino acid residues linked to each other via peptide linkages. The peptide of the present invention may be prepared by chemical synthesis methods known in the art, especially, solid-phase synthesis techniques (solid-phase synthesis techniques; Merrifield, *J. Amer. Chem. Soc.* 85:2149-54(1963); Stewart, et al., *Solid Phase Peptide Synthesis*, 2nd. ed., Pierce Chem. Co.: Rockford, 111(1984)) or liquid-phase synthesis techniques (U.S. Pat. No. 5,516,891).

The peptide of the present invention is obtained by screening peptides, which have excellent efficacy of hair production, from peptide libraries possessed by the present inventors, through cell proliferation experiments, and a total of three types of peptides are provided as a peptide of the present invention.

The peptide of the present invention may have a modification induced at the N-terminal and/or C-terminal thereof in order to select a part of an amino acid sequence and increase the activity thereof.

For example, the C-terminal modification may be a modification of the C-terminal of the peptide into a hydroxy group (—OH), an amino group (—NH$_2$), an azide group (—NHNH$_2$), or the like, but is not limited thereto.

In addition, the N-terminal modification may be an attachment of at least one protecting group selected from the group consisting of an acetyl group, a fluorenyl methoxy carbonyl group, a formyl group, a palmitoyl group, a myristyl group, a stearyl group, and polyethylene glycol (PEG) to the N-terminal of the peptide, but is not limited thereto. The protecting group protects the peptide of the present invention from in vivo protein cleavage enzymes.

The N-terminal and/or C-terminal modification of the peptide improves the stability of the peptide, and this modification allows the peptide of the present invention to have an increased half-life at the time of in vivo administration, thereby having a high half-life.

As used herein, the term "stability" refers to storage stability (e.g., room-temperature stability) as well as in vivo stability.

As used herein, the term "hair production stimulating" refers to the production of hair, and is used in a broad sense to increase the rate of hair production and the amount of hair production. In addition, the term means that hair root functions are enhanced, or the number of hairs growing in hair follicles increases due to shortening the cycle of hair falling and production.

As used herein, the term "hair growth" refers to increasing the thickness of the generated hair or having an influence on the length increase rate.

According to another aspect of the present invention, the peptides of the present invention stimulate the growth of hair follicle cells, increase the expression of β-catenin as a hair growth-related factor, increase the expression of keratinocyte growth factor (KGF), basic fibroblast growth factor (bFGF), and vascular endothelial growth factor (VEGF) as hair growth-related growth factors, increase the expression of phosphoinositide 3-kinase (PI3K) as a hair growth signaling molecule, increase the phosphorylation of extracellular signal-regulated kinase (ERK), increase the expression of MSX2 and keratin-14 as hair growth-related factors, inhibit the expression of TGF-β1 as hair growth delay, increase the expression of Bcl-2 as an apoptosis inhibiting protein, and induces the reduction of the expression of Bax as an apoptosis-related protein.

These results indicate that the peptides of the present invention have a very excellent effect in the hair production and/or hair growth. Therefore, the peptides of the present invention can be used for the prevention and/or relief of hair loss and the stimulation of hair production and/or hair growth.

Still another aspect of the present invention is directed to a composition for preventing or improving hair loss, the composition containing a peptide of the present invention as an active ingredient.

As used herein, the term "preventing hair loss" refers to blocking or reducing hair loss from the hair follicles or scalp.

The peptides of the present invention induce the proliferation of cells present in hair follicles of skin tissue so as to produce hair roots, leading to the production of new hair follicles. Furthermore, the peptide of the present invention activates β-catenin signals to express hair production stimulating genes and increase the expression of growth factors.

The peptide of the present invention promotes the anagen phase during which hair is produced and grown, exhibits a hair loss inhibiting effect by maintaining the cycle of hair, which proceeds to the catagen phase due to several environmental factors, at the anagen phase, and keeps healthy hair by providing nutrients to normal hair. Therefore, the composition of the present invention is very effective in the prevention and/or relief of hair loss.

Since the composition of the present invention contains the foregoing peptide of the present invention as an active ingredient, the descriptions of overlapping contents therebetween will be omitted to avoid excessive complexity of the present specification.

In accordance with still another aspect of the present invention, there is provided a composition for stimulating hair production and/or hair growth, the composition comprising, as an active ingredient, at least one peptide selected from the group consisting of peptides consisting of the amino acid sequence selected from the group consisting of SEQ ID NO: 1 to SEQ ID NO: 3.

The composition of the present invention may be prepared into a cosmetic composition, but is not limited thereto.

The cosmetic composition of the present invention may contain a cosmetically effective amount of the peptide of the present invention.

In addition, the cosmetic composition may further contain a cosmetically acceptable carrier, but is not limited thereto.

As used herein, the term "cosmetically effective amount" refers to an amount sufficient to attain the efficacy of the foregoing cosmetic composition of the present invention.

The cosmetic composition of the present invention may be formulated into any dosage form that is conventionally prepared, and examples thereof may include a solution, a suspension, an emulsion, a paste, a gel, a cream, a lotion, a powder, a soap, a surfactant-containing cleanser, an oil, a powder foundation, an emulsion foundation, a wax foundation, and a spray, but are not limited thereto. For example, the cosmetic composition of the present invention may be prepared in a dosage form of emollient lotion, nourishing lotion, nourishing cream, massage cream, essence, eye cream, cleansing cream, cleansing foam, cleansing water, pack, spray, and/or powder.

In cases where the dosage form of the cosmetic composition is a paste, cream, or gel, useful examples of the carrier ingredient may include an animal oil, a plant oil, wax, paraffin, starch, tragacanth, a cellulose derivative, polyethylene glycol, silicone, bentonite, silica, talc, or zinc oxide, but is not limited thereto.

In cases where the dosage form of the cosmetic composition is a powder or spray, lactose, talc, silica, aluminum hydroxide, calcium silicate, or a polyamide powder may be used as a carrier ingredient, but is not limited thereto. Especially, in cases where the dosage form of the present invention is a spray, the spray may further include a propellant, such as chlorofluorohydrocarbon, propane/butane, or dimethyl ether, but is not limited thereto.

In cases where the dosage form of the cosmetic composition is a solution or emulsion, a solvent, solubilizer, or emulsifier may be used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic esters, polyethylene glycol, or fatty acid esters of sorbitan.

In cases where the dosage form of the cosmetic composition is a suspension, useful examples of the carrier ingredient may include a liquid diluent (such as water, ethanol, or propylene glycol), a suspending agent (such as ethoxylated isostearyl alcohol, polyoxyethylene sorbitol ester, or polyoxyethylene sorbitan ester), microcrystalline cellulose, aluminum metahydroxide, bentonite, agar, or tragacanth, but are not limited thereto.

In cases where the dosage form of the cosmetic composition is a surfactant-containing cleanser, useful examples of the carrier ingredient may be aliphatic alcohol sulfate, aliphatic alcohol ether sulfate, sulfosuccinate monoester, isethionate, imidazolium derivatives, methyl taurate, sarcosinate, fatty acid amide ether sulfate, alkyl amido betaine, aliphatic alcohol, fatty acid glyceride, fatty acid diethanolamide, plant oil, lanoline derivatives, or ethoxylated glycerol fatty acid ester, but are not limited thereto.

The ingredients contained in the cosmetic composition of the present invention may include, in addition to the peptide and carrier ingredients as active ingredients, ingredients ordinarily used in cosmetic compositions, for example, ordinary supplements, such as an antioxidant, a purifier, a solubilizer, vitamins, a pigment and/or a flavoring agent, but are not limited thereto.

In accordance with still another aspect of the present invention, there is provided a use of a peptide consisting of the amino acid sequence selected from the group consisting of SEQ ID NO: 1 to SEQ ID NO: 3 for preventing and/or relieving hair loss.

Since the peptide is the same as the foregoing peptide, the descriptions of overlapping contents therebetween will be omitted to avoid excessive complexity of the present specification.

In accordance with still another aspect of the present invention, there is provided a use of a peptide consisting of the amino acid sequence selected from the group consisting of SEQ ID NO: 1 to SEQ ID NO: 3 for stimulating hair production and/or hair growth.

Since the peptide is the same as the foregoing peptide, the descriptions of overlapping contents therebetween will be omitted to avoid excessive complexity of the present specification.

Advantageous Effects

The present invention relates to a peptide having an activity to stimulate hair production and/or hair growth, to a composition containing the peptide as an active ingredient for preventing and/or improving hair loss, to a composition containing the peptide as an active ingredient for stimulating hair production and/or hair growth, to a use of the peptide for preventing and/or improving hair loss, and to a use of the peptide for stimulating hair production and/or hair growth. The peptide stimulates hair follicle cells growth and increases the expression of hair production-related growth factors and hair production-related factors, thereby having excellent effects on hair production and/or hair growth, and thus the peptide can be vary advantageously applied to cosmetic products through excellent activity and safety thereof.

BRIEF DESCRIPTION OF THE DRAWINGS

FIG. 1b is a graph showing a human hair follicle dermal papilla cell (HHFDPC) growth stimulating effect of a peptide composed of the amino acid sequence of SEQ ID NO: 2 according to an embodiment of the present invention.

FIG. 1c is a graph showing a human hair follicle dermal papilla cell (HHFDPC) growth stimulating effect of a peptide composed of the amino acid sequence of SEQ ID NO: 3 according to an embodiment of the present invention.

FIG. 2a is a diagram showing the results of confirming the increase of β-catenin expression by a peptide composed of the amino acid sequence of SEQ ID NO: 1 according to an embodiment of the present invention.

FIG. 2c is a diagram showing the results of confirming the increase of β-catenin expression by a peptide composed of the amino acid sequence of SEQ ID NO: 3 according to an embodiment of the present invention.

FIG. 3a is an image showing the results of confirming the increases of KGF and bFGF expression by a peptide composed of the amino acid sequence of SEQ ID NO: 1 according to an embodiment of the present invention.

FIG. 3c is a diagram showing the results of confirming the increase of VEGF and bFGF expression by a peptide composed of the amino acid sequence of SEQ ID NO: 3 according to an embodiment of the present invention.

FIG. 4a is an image showing the results of confirming the increase of PI3K expression and the increase of ERK phosphorylation by a peptide composed of the amino acid sequence of SEQ ID NO: 1 according to an embodiment of the present invention.

FIG. 4c is an image showing the results of confirming the increase of PI3K expression and the increase of ERK phosphorylation by a peptide composed of the amino acid sequence of SEQ ID NO: 3 according to an embodiment of the present invention.

FIG. 5a is an image showing the results of confirming the increase of MSX2 expression by a peptide composed of the amino acid sequence of SEQ ID NO: 2 according to an embodiment of the present invention.

FIG. 6a is an image showing the results of confirming the inhibition of TGF-$\beta$1 expression by a peptide composed of the amino acid sequence of SEQ ID NO: 1 according to an embodiment of the present invention.

FIG. 7a is an image showing the results of confirming the increase of Bcl-2 expression and the increase in Bax expression by a peptide composed of the amino acid sequence of SEQ ID NO: 1 according to an embodiment of the present invention.

FIG. 7b is an image showing the results of confirming the increase of Bcl-2 expression and the increase of Bax expression by a peptide composed of the amino acid sequence of SEQ ID NO: 3 according to an embodiment of the present invention.

BEST MODE FOR CARRYING OUT THE INVENTION

Figure 1A:
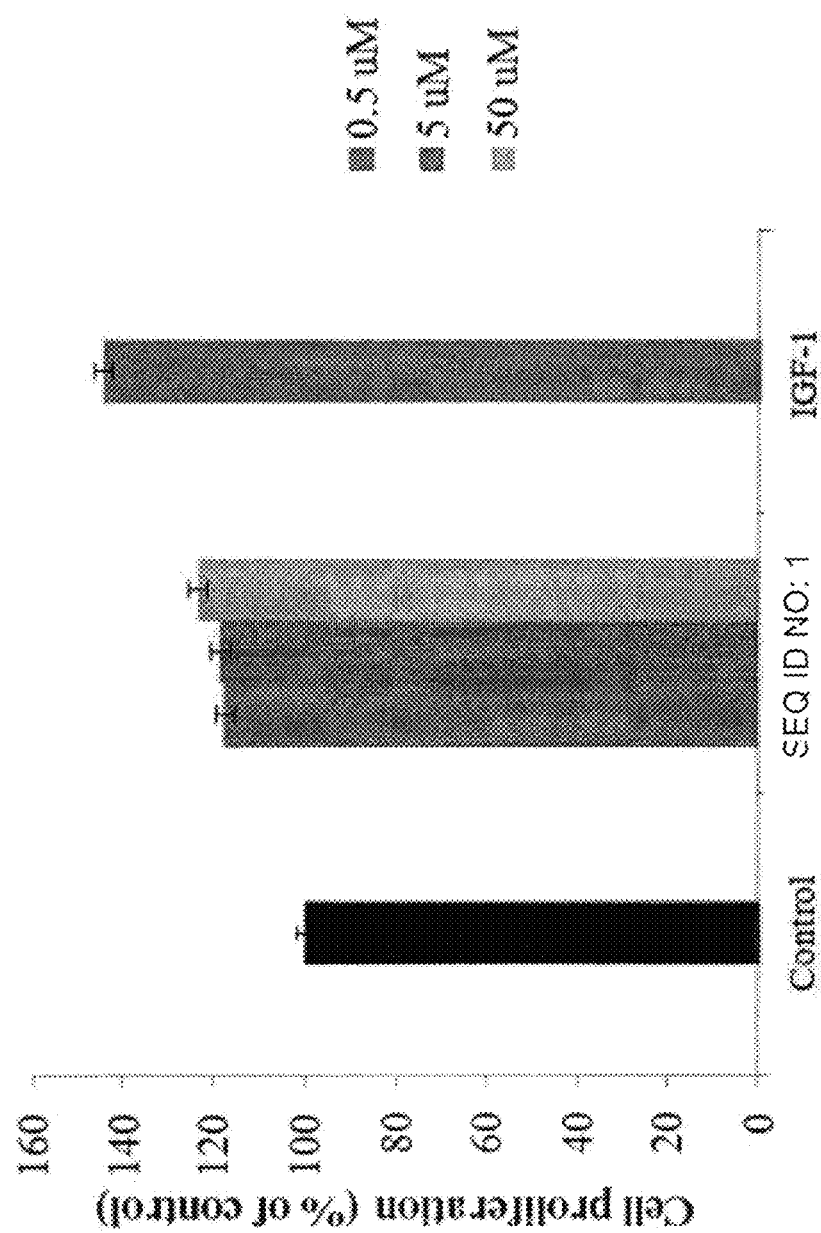
FIG. 1a is a graph showing a human hair follicle dermal papilla cell (HHFDPC) growth stimulating effect of a peptide composed of the amino acid sequence of SEQ ID NO: 1 according to an embodiment of the present invention.

The present invention relates to a peptide having an activity to stimulate hair production, the peptide consisting of the amino acid sequence selected from SEQ ID NO: 1 to SEQ ID NO: 3.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Synthetic Example 1

Peptide Synthesis 700 mg of chlorotrityl chloride resin (CTL resin, Nova Biochem Cat No. 01-64-0021) was added into a reaction container, and 10 ml of methylene chloride (MC) was added, followed by stirring for 3 minutes. After the solution was removed, 10 ml of dimethyl form amide (DMF) was added, followed by stirring for 3 minutes, and then the solvent was again removed.

10 ml of a dichloromethane solution was added to a reactor, and 200 mmole Fmoc-Ile-OH (Bachem, Swiss) and 400 mmole diisopropyl ethylamine (DIEA) were added. Thereafter, the mixture was well dissolved with stirring, and then the reaction was conducted with stirring for 1 hour.

After the reaction, washing was conducted, and then methanol and DIEA (2:1) were dissolved in dichloromethane (DCM), followed by reaction for 10 minutes, and then the resulting material was washed with excess DCM/DMF (1:1). After the solution was removed, 10 ml of dimethyl form amide (DMF) was added, followed by stirring for 3 minutes, and then the solvent was again removed.

10 ml of a deprotection solution (20% piperidine/DMF) was added to a reaction container, followed by stirring at room temperature for 10 minutes, and then the solution was removed. An equal amount of a deprotection solution was added, and then the reaction was again maintained for 10 minutes, and thereafter, the solution was removed, followed by washing twice with DMF, once with MC, and once with DMF, for 3 minutes each, thereby preparing Ile-CTL Resin.

10 ml of a DMF solution was added to a new reactor, and 200 mmol Fmoc-Lys(Boc)-OH (Bachem, Swiss), 200 mmol HoBt, and 200 mmole Bop were added, and the mixture was well dissolved with stirring. 400 mmole DIEA was added to a reactor in two divided portions, and then stirring was conducted for at least 5 minutes until all solids were dissolved.

The dissolved amino acid mixed solution was added to the reaction container containing the deprotected resin, and the reaction was conducted with stirring at room temperature for 1 hour. After the reaction solution was removed, the stirring was conducted using a DMF solution three times for 5 minutes each, followed by removal.

A small amount of the reaction resin was taken to check the extent of reaction using the Kaiser test (Ninhydrin test). The deprotection reaction was twice conducted using a deprotection solution in the same manner as described above, thereby preparing Lys(Boc)-Ile-CTL Resin.

After sufficient washing with DMF and MC, the Kaiser test was again conducted, and then the following amino acid attachment test was conducted in the same manner as described above.

A chain reaction was conducted in the order of Fmoc-Arg(Pbf)-OH and Fmoc-Arg(Pbf)-OH on the basis of the selected amino acid sequence. The Fmoc-protecting group was removed by reaction twice with the deprotection solution for 10 minutes for each and then favorable washing.

Acetic anhydride, DIEA, and HoBt were added to conduct acetylation for 1 hour, and then the prepared peptidyl resin was washed with DMF, MC, and methanol three times for each, dried under the flow of nitrogen gas, and completely dried by decompression under vacuum in $P_2O_5$.

Thereafter, 30 ml of a leaving solution [95% trifluoroacetic acid (TFA), 5% distilled water 2, and 5% thioanisole 2] was added, and the reaction was maintained for 2 hours while the mixture was intermittently stirred at room temperature.

The resin was obtained through filtration, washed with a small amount of a TFA solution, and then mixed with the stock solution. The distillation was conducted under reduced pressure to reduce the total volume by half, and then 50 ml of cold ether was added to induce precipitation.

Thereafter, the precipitates were collected by centrifugation, followed by washing twice with cold ether. The stock solution was removed, followed by sufficient drying under nitrogen atmosphere, thereby synthesizing 0.7 g of unpurified peptide 1, Arg-Arg-Lys-Ile (yield: 90.0%).

The molecular weight was determined as 571.7 (theoretical value: 571.72) by using a molecular weight analysis system.

The other peptides, peptide 2 composed of the amino acid sequence of SEQ ID NO: 2 and peptide 3 composed of the amino acid sequence of SEQ ID NO: 3 were also synthesized by the same method as described above.

TABLE 1

| SEQ ID NO | Sequence (5'-3') | Molecular weight analysis value (Mass spectromter) | |
|---|---|---|---|
| | | Analytic value | Theoretical value |
| 1 | Arg-Arg-Lys-Ile | 571.7 | 571.72 |
| 2 | Ile-Tyr-Phe-Tyr | 604 | 604.7 |
| 3 | Lys-Lys-Phe-Ile-Gln-Gln-Val-Tyr-Leu-Ala-Ile | 1350.6 | 1350.65 |

In order to secure peptides showing hair growth stimulating efficacy, screening was conducted for the peptide libraries of the applicant through cell proliferation experiments, and thus three types of peptides were selected. Thereafter, the hair growth stimulating efficacy of the three types of peptides was observed through the expression changes of various genes and proteins, and the excellent efficacy thereof was investigated.

Example 1

DPC Proliferation Assay

Human hair follicle dermal papilla cells were seeded at a density of $2\times10^3$ cells/well on 96-well plates, followed by incubation overnight. After changing into serum-free medium, the cells were treated with the peptides, followed by incubation for 3 days, and then the wells were treated with 4 mg/ml MTT solution, followed by reaction for 4 hours. The resulting formazan was solubilized with DNSO, and then the absorbance was measured at 550 nm using a microplate reader. The results are shown in FIGS. 1a to 1c.

As can be confirmed from FIGS. 1a to 1c, the growth of human hair follicle dermal papilla cells were stimulated in a dose-dependent manner by the treatment of the peptide composed of the amino acid sequence of SEQ ID NO: 1, SEQ ID NO: 2, or SEQ ID NO: 3, respectively.

Example 2

β-Catenin Activation Test

Human hair follicle dermal papilla cells were seeded at a density of $4\times10^5$ cells/well on 6-well plates, followed by incubation overnight. After changing into serum-free medium, the cells were treated with the peptides, followed by incubation for 15 and 30 minutes, and then the wells were harvested to isolate nuclear and cytoplasmic proteins. Western blotting was performed using β-catenin (Santa Cruz Biotechnology, USA) to compare β-catenin expression patterns in nuclei. The results are shown in FIGS. 2a to 2c.

Figure 2B:
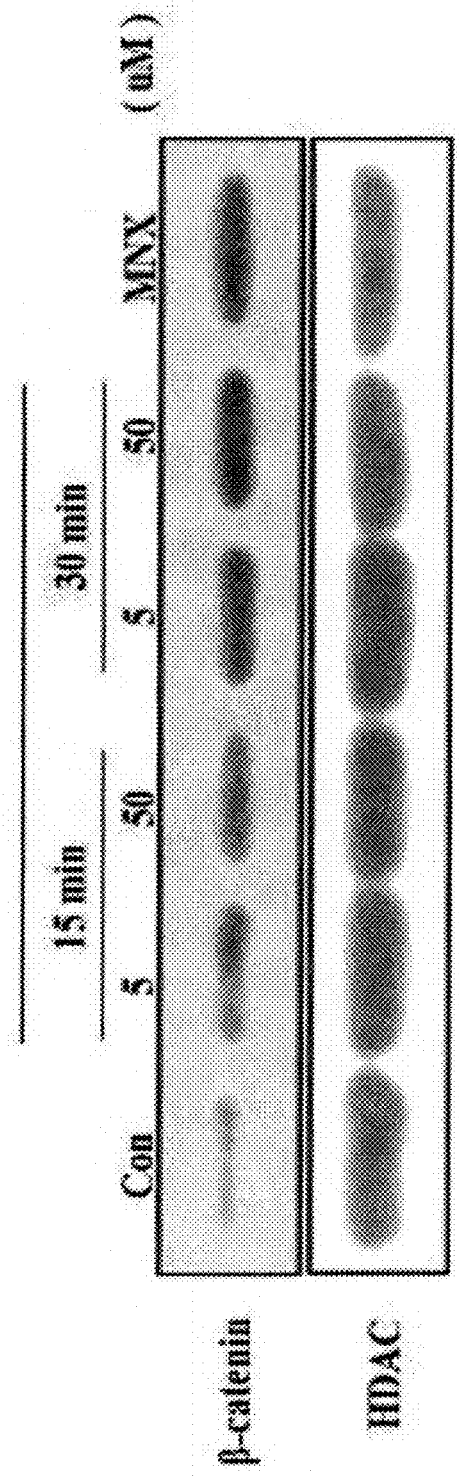
FIG. 2b is a diagram showing the results of confirming the increase of β-catenin expression by a peptide composed of the amino acid sequence of SEQ ID NO: 2 according to an embodiment of the present invention.

As can be confirmed from FIGS. 2a to 2c, it was observed that the nuclear translocation due to the increase in activity of β-catenin, which is a hair growth-related factor, was stimulated by the treatment with the peptide composed of the amino acid sequence of SEQ ID NO: 1, SEQ ID NO: 2, or SEQ ID NO: 3.

Example 3

KGF, bFGF, VEGF RT-PCR

Figure 3B:
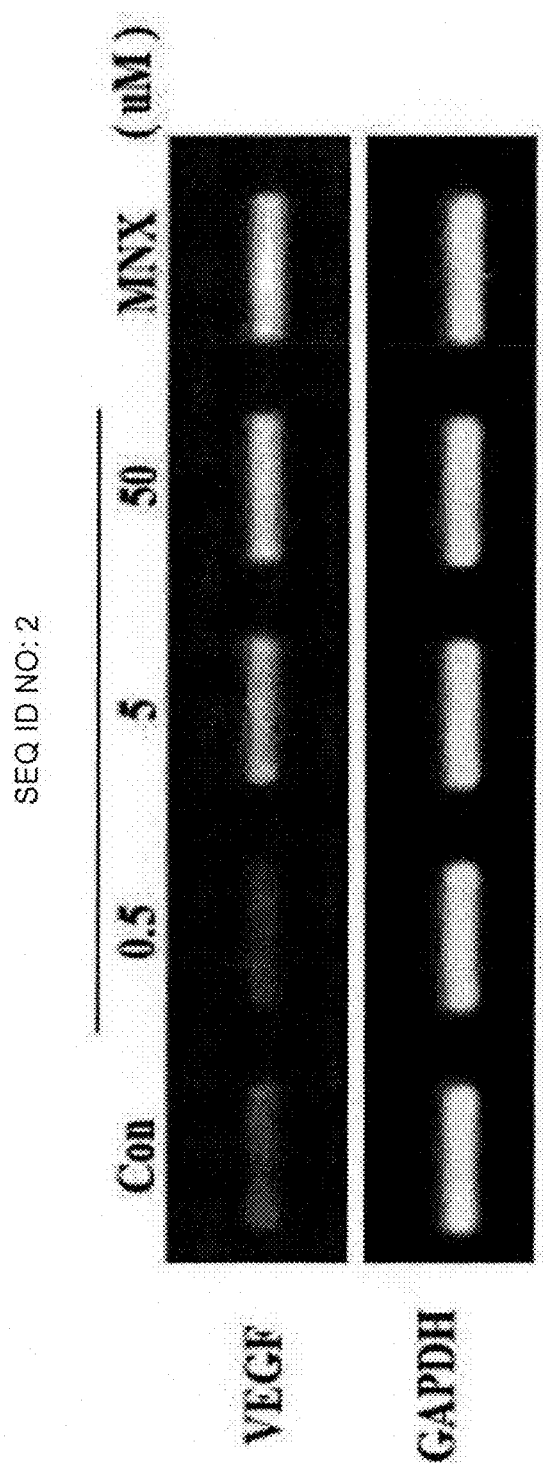
FIG. 3b is a diagram showing the results of confirming the increase of VEGF expression by a peptide composed of the amino acid sequence of SEQ ID NO: 2 according to an embodiment of the present invention.

Human hair follicle dermal papilla cells were seeded at a density of $4\times10^5$ cells/well on 6-well plates, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and respective KGF, bFGF, and VEGF primers, and then electrophoresis was performed on 5% agarose gel to compare the mRNA expression levels of the growth factors for each sample treatment conditions. The results are shown in FIGS. 3a to 3c.

TABLE 2

| SEQ ID NO | Primer nomenclature | Sequence (5'-3') |
|---|---|---|
| 4 | KGF_F | TCTGTCGAACACAGTGGTACCT |
| 5 | KGF_R | GTGTGTCCATTTAGCTGATGCAT |
| 6 | bFGF_F | TGCTGGTGATGGGAGTTGTA |
| 7 | bFGF_R | CCTCCAAGTAGCAGCCAAAG |
| 8 | VEGF_F | CCATGAACTTTCTGCTGTCTT |
| 9 | VEGF_R | TCGATCGTTCTGTATCAGTCT |

As can be confirmed from FIG. 3a, the mRNA expression of KGF and bFGF, which are growth factors involved in hair growth in human hair follicle dermal papilla cells, was increased by the treatment with the peptide composed of the amino acid sequence of SEQ ID NO: 1.

As can be confirmed from FIG. 3b, the mRNA expression of VEGF, which is a factor influencing hair growth in human hair follicle dermal papilla cells, was increased by the treatment with the peptide composed of the amino acid sequence of SEQ ID NO: 2. As can be confirmed from FIG. 3c, the mRNA expression of VEGF and bFGF was increased by the treatment with the peptide composed of the amino acid sequence of SEQ ID NO: 3.

Example 4

PI3K & p-ERK WB

Human hair follicle dermal papilla cells were seeded at a density of $4\times10^5$ cells/well on 6-well plates, followed by incubation overnight. After changing into serum-free medium, the cells were treated with the peptides, followed by incubation for 15 and 30 minutes, and then the wells were harvested to prepare cell lysates. Western blotting was performed using PI3K antibodies (Santa Cruz Biotechnology, USA) and phospho-ERK antibody (Cell Signaling Technology, USA) to compare protein expression patterns. The results are shown in FIGS. 4a and 4b.

Figure 4B:
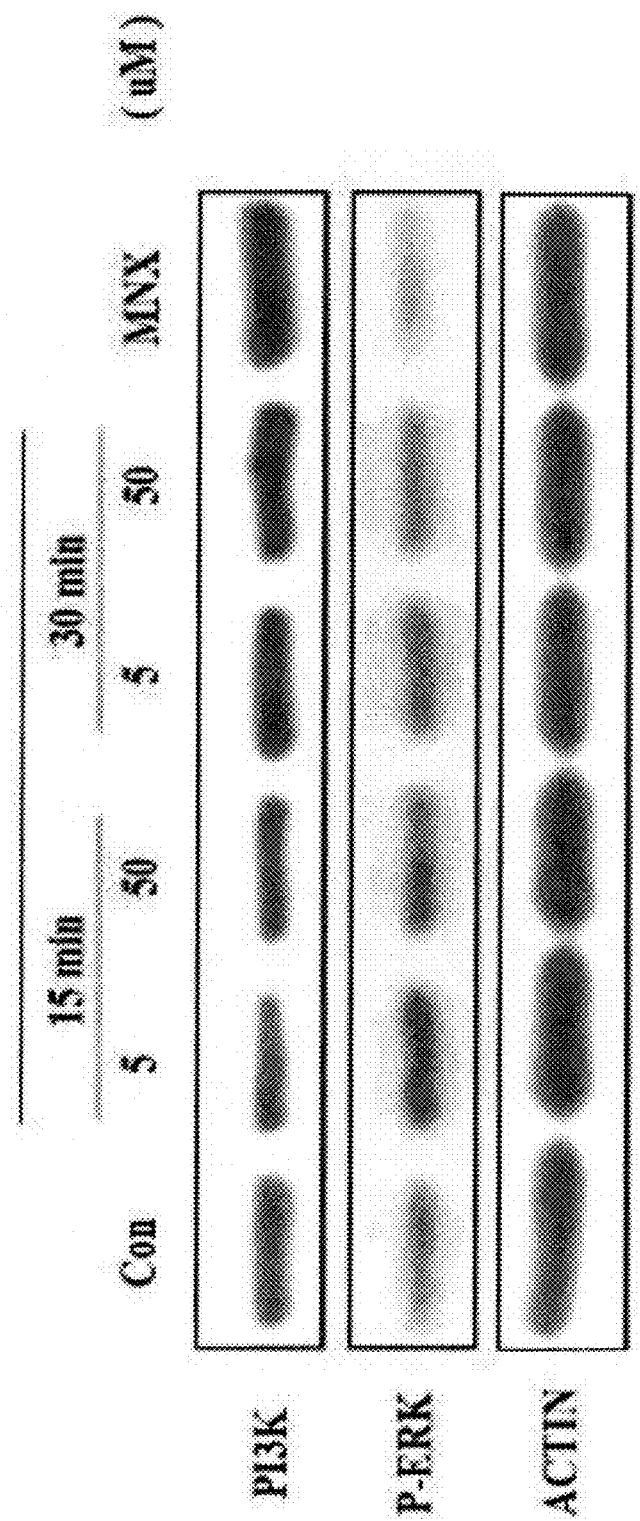
FIG. 4b is an image showing the results of confirming the increase of PI3K expression and the increase of ERK phosphorylation by a peptide composed of the amino acid sequence of SEQ ID NO: 2 according to an embodiment of the present invention.

As can be confirmed from FIGS. 4a and 4b, the increase of PI3K expression and the increase of ERK phosphorylation, which are hair growth signaling molecules in human hair follicle dermal papilla cells, were observed by the treatment with the peptide composed of the amino acid sequence of SEQ ID NO: 1 or SEQ ID NO: 3.

Example 5

MSX2 RT-PCR

Human hair follicle dermal papilla cells were seeded at a density of 4×10⁵ cells/well on 6-well plates, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and MSX2 primers, and then electrophoresis was performed on 5% agarose gel to compare the mRNA expression levels for each sample treatment conditions. The results are shown in FIGS. 5a and 5b.

TABLE 3

| SEQ ID NO | Primer nomenclature | Sequence (5'-3') |
|---|---|---|
| 10 | MSX2_F | AACACAAGACCAACCGGAAG |
| 11 | MSX2_R | GCAGCCATTTTCAGCTTTTC |

Figure 5B:
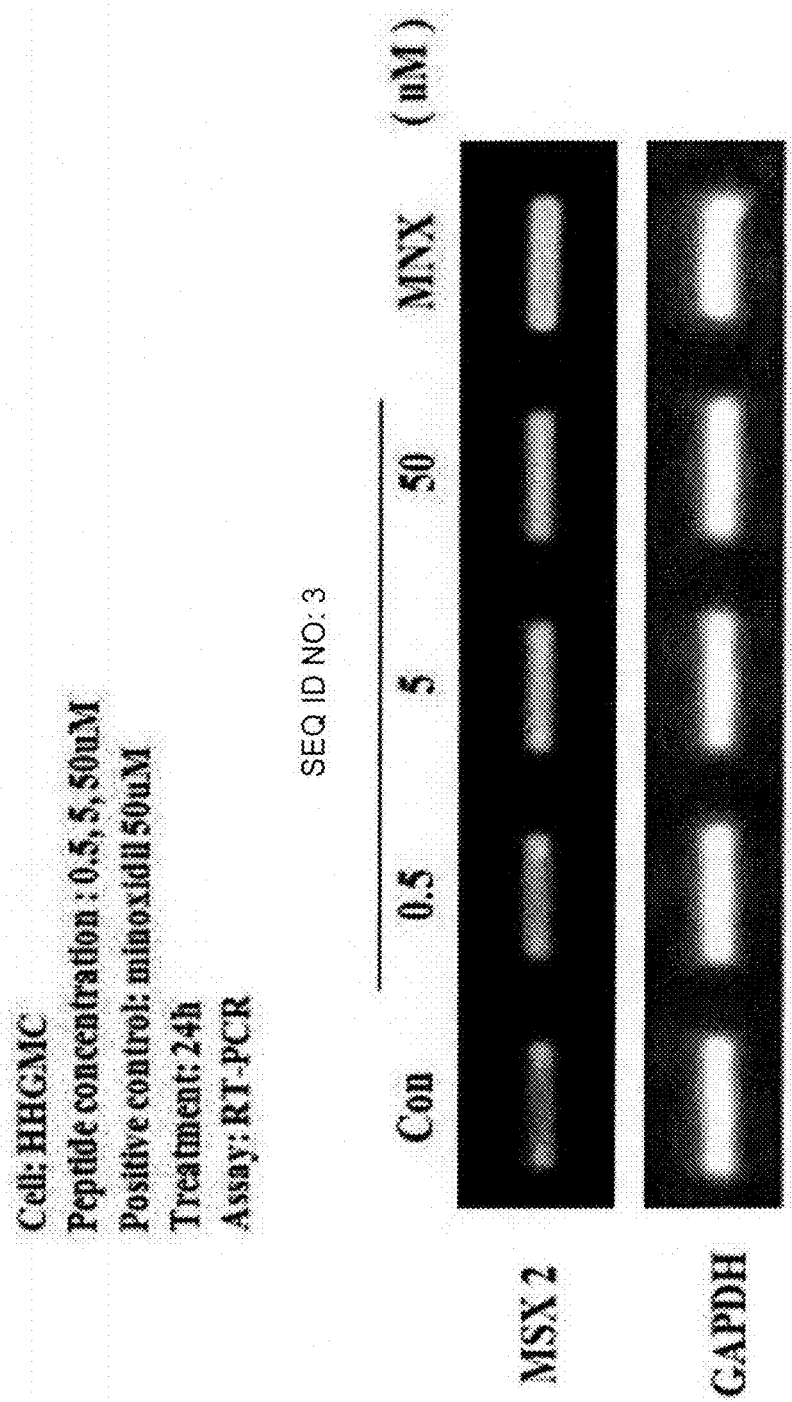
FIG. 5b is an image showing the results of confirming the increase of MSX2 expression by a peptide composed of the amino acid sequence of SEQ ID NO: 3 according to an embodiment of the present invention.

As can be seen from FIGS. 5a and 5b, the mRNA expression of MSX2, which is a hair growth-related factor in human hair follicle dermal papilla cells, was stimulated by the treatment with the peptide composed of the amino acid sequence of SEQ ID NO: 2 or SEQ ID NO: 3.

Example 6

TGF-β1 RT-PCR

Human hair follicle dermal papilla cells were seeded at a density of 4×10⁵ cells/well on 6-well plates, followed by incubation overnight. After changing into serum-free medium, the cells were treated with the peptides, followed by incubation for 24 hours, and then the wells were harvested to separate RNA. After RNA quantification, cDNA synthesis was conducted using the cDNA synthesis kit (Intron, Korea), followed by PCR using PCR premix (Intron, Korea) and TGF-β1 primers, and then electrophoresis was performed on 5% agarose gel to compare the mRNA expression levels for each sample treatment conditions. The results are shown in FIGS. 6a and 6b.

TABLE 4

| SEQ ID NO | primer nomenclature | Sequence (5'-3') |
|---|---|---|
| 12 | TGF-β1_F | GCCCTGGATACCAACTATTGC |
| 13 | TGF-β1_R | TCAGCACTTGCAGGAGTAGCG |

Figure 6B:
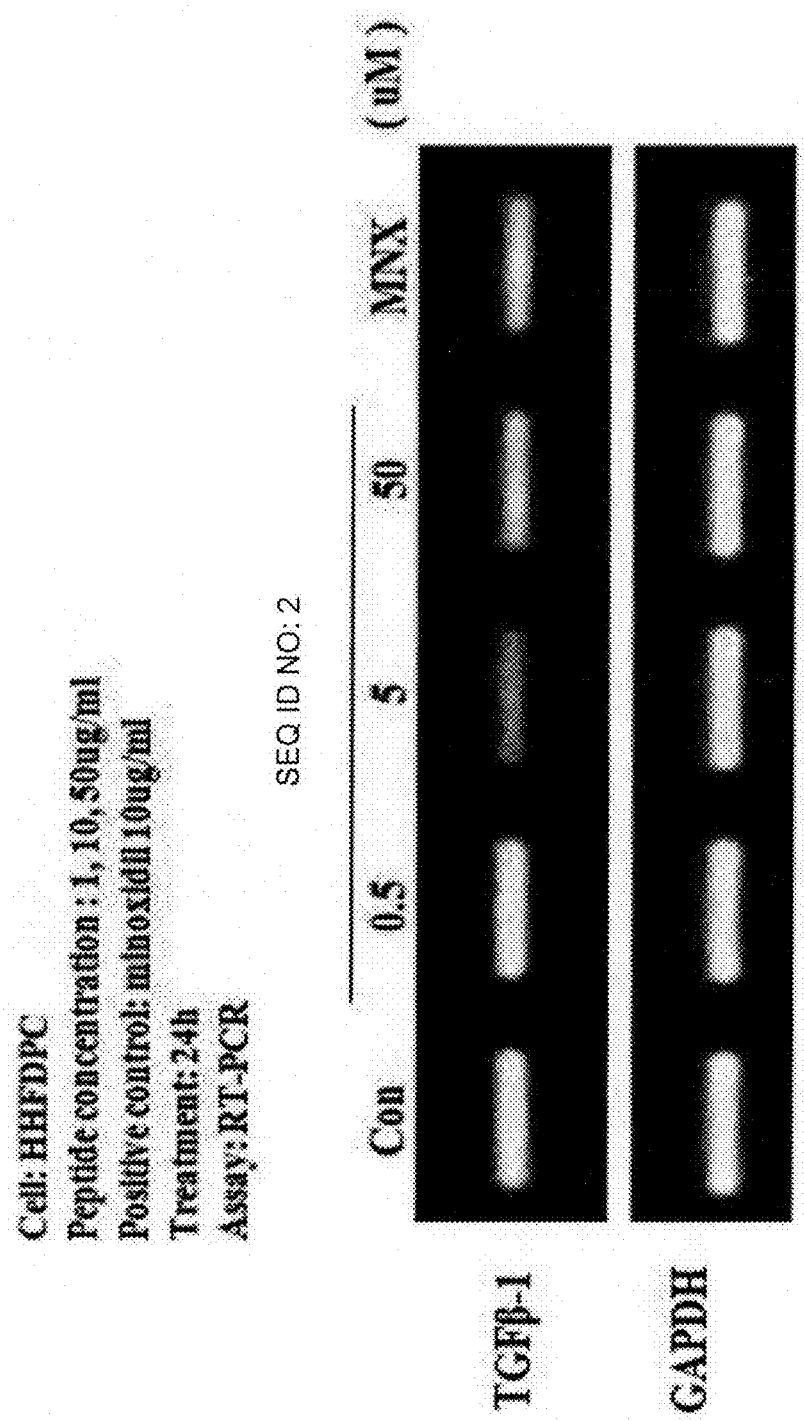
FIG. 6b is an image showing the results of confirming the inhibition of TGF-$\beta$1 expression by a peptide composed of the amino acid sequence of SEQ ID NO: 2 according to an embodiment of the present invention.

As can be seen from FIGS. 6a and 6b, the mRNA expression of TGF-β1, which is a hair growth delay-related factor in human hair follicle dermal papilla cells, was inhibited by the treatment with the peptide composed of the amino acid sequence of SEQ ID NO: 1 or SEQ ID NO: 2.

Example 7

Bcl-2/Bax WB

Human hair follicle dermal papilla cells were seeded at a density of 4×10⁵ cells/well on 6-well plate, followed by incubation overnight. After changing into serum-free medium, the cells were treated with the peptides, followed by incubation for 24 hours, and then the wells were harvested to prepare cell lysates. Western blotting was performed using Bcl-2 and Bax antibodies (Santa Cruz Biotechnology, USA) to compare protein expression patterns. The results are shown in FIGS. 7a and 7b.

As can be confirmed from FIGS. 7a and 7b, the expression increase of the apoptosis inhibiting protein Bcl-2 and the expression decrease of the apoptosis-related protein Bax in human hair follicle dermal papilla cells were observed by the treatment with the peptide composed of the amino acid sequence of SEQ ID NO: 1 or SEQ ID NO: 3.

Example 8

Keratin-14 RT-PCR

Human hair follicle dermal papilla cells were seeded at a density of 5×10⁵ cells/well on 6-well plates, followed by incubation overnight. After changing into serum-free medium, the cells were treated with the peptides, followed by incubation for 24 hours, and then the wells were harvested to isolate RNA. After RNA quantification, cDNA synthesis was conducted using the cDNA synthesis kit (Intron, Korea), followed by PCR using PCR premix (Intron, Korea) and keratin primers, and then electrophoresis was performed on 5% agarose gel to compare the mRNA expression levels for respective sample treatment conditions. The results are shown in FIG. 8.

TABLE 5

| SEQ ID NO | primer nomenclature | Sequence (5'-3') |
|---|---|---|
| 14 | Keratin-14_F | CCACCTTTCATCTTCCCAATTCTC |
| 15 | Keratin-14_R | GTGCGGATCTGGCGGTTG |

Figure 8:
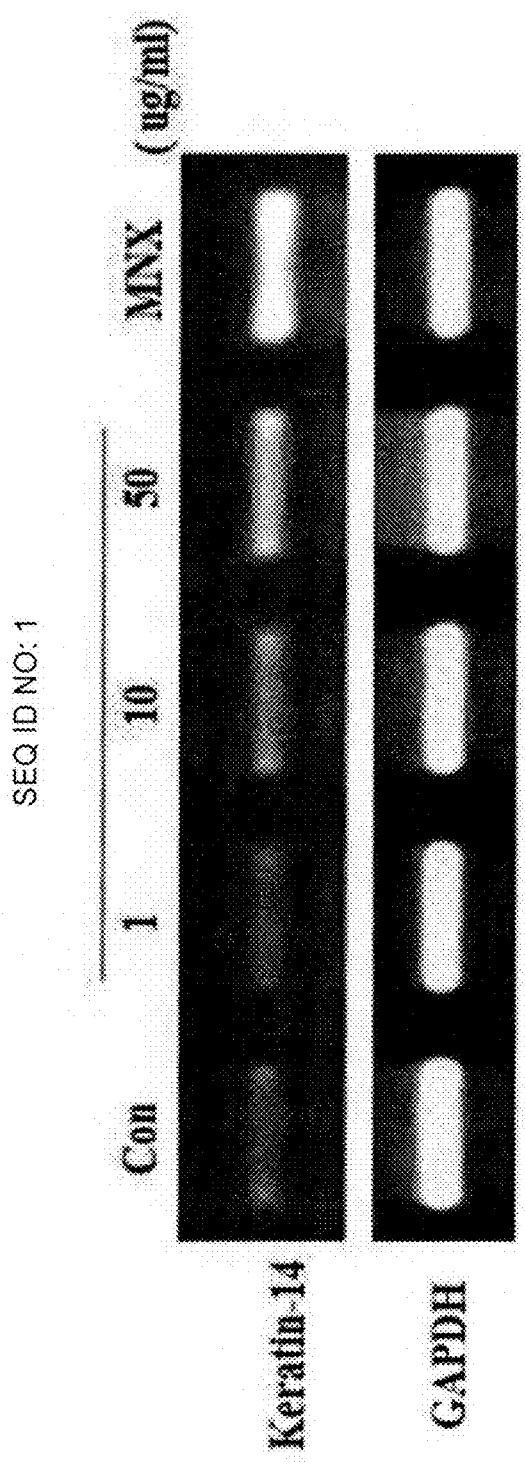
FIG. 8 is an image showing the results of confirming the increase of keratin-14 expression by a peptide composed of the amino acid sequence of SEQ ID NO: 1 according to an embodiment of the present invention.

As can be confirmed from FIG. 8, the mRNA expression of keratin-14, which is a hair growth-related factor in human hair follicle dermal papilla cells, was increased by the treatment with the peptide composed of the amino acid sequence of SEQ ID NO: 1.

INDUSTRIAL APPLICABILITY

The present invention relates to a peptide having an activity to stimulate hair production and/or growth, a composition containing the peptide as an active ingredient for stimulating hair production, and a use of the peptide for stimulating hair production.

The invention claimed is:

1. A peptide having an activity to stimulate hair production, the peptide consisting of the amino acid sequence selected from the group consisting of SEQ ID NO: 1, SEQ ID NO: 2, or SEQ ID NO: 3 optionally wherein (i) the C-terminal end of the peptide is modified by the presence of an amino group or an azide group, or (ii) the N-terminal end of the peptide comprises a protecting group.

2. The peptide of claim 1, wherein the peptide stimulates the growth of hair follicle cells.

3. The peptide of claim 1, wherein the peptide increases the expression of β-catenin.

4. A method for preventing or improving hair loss comprising:
   administering a composition comprising at least one peptide selected from the peptide consisting of the amino acid of SEQ ID NO: 1, peptide consisting of the amino acid of SEQ ID NO: 2 and peptide consisting of the amino acid of SEQ ID NO: 3, as an active ingredient, optionally wherein (i) the C-terminal end of the peptide is modified by the presence of an amino group or an azide group, or (ii) the N-terminal end of the peptide comprises a protecting group.

5. A method for stimulating hair production or hair growth comprising:
   administering a composition comprising at least one peptide selected from the peptide consisting of the amino acid of SEQ ID NO: 1, peptide consisting of the amino acid of SEQ ID NO: 2 and peptide consisting of the amino acid of SEQ ID NO: 3, as an active ingredient, optionally wherein (i) the C-terminal end of the peptide is modified by the presence of an amino group or an azide group, or (ii) the N-terminal end of the peptide comprises a protecting group.

6. The peptide of claim 1, wherein the C-terminal end of the peptide is modified by the presence of an amino group or an azide group.

7. The peptide of claim 1, wherein the N-terminal end of the peptide comprises a protecting group.

8. The peptide of claim 7, wherein the protecting group is selected from the group consisting of an acetyl group, a fluorenyl methoxy carbonyl group, a formyl group, a palmitoyl group, a myristyl group, a stearyl group, and polyethylene glycol (PEG).

9. The method of claim 4, wherein the C-terminal end of the peptide is modified by the presence of an amino group or an azide group.

10. The method of claim 4, wherein the N-terminal end of the peptide comprises a protecting group.

11. The method of claim 10, wherein the protecting group is selected from the group consisting of an acetyl group, a fluorenyl methoxy carbonyl group, a formyl group, a palmitoyl group, a myristyl group, a stearyl group, and polyethylene glycol (PEG).

12. The method of claim 5, wherein the C-terminal end of the peptide is modified by the presence of an amino group or an azide group.

13. The method of claim 5, wherein the N-terminal end of the peptide comprises a protecting group.

14. The method of claim 13, wherein the protecting group is selected from the group consisting of an acetyl group, a fluorenyl methoxy carbonyl group, a formyl group, a palmitoyl group, a myristyl group, a stearyl group, and polyethylene glycol (PEG).

\* \* \* \* \*

SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Arg Arg Lys Ile
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Construct

<400> SEQUENCE: 2

Ile Tyr Phe Tyr
1

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Lys Lys Phe Ile Gln Gln Val Tyr Leu Ala Ile
1               5                   10

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct

<400> SEQUENCE: 4
tctgtcgaac acagtggtac ct                                        22

<210> SEQ ID NO 5
<211> LENGTH: 23
<212> TYPE: DNA
<213> ORGANISM: Artificial Sequence
<220> FEATURE:
<223> OTHER INFORMATION: Synthetic Construct

<400> SEQUENCE: 5
gtgtgtccat ttagctgatg cat                                       23

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tgctggtgat gggagttgta                                           20

<210> SEQ ID NO 7

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
cctccaagta gcagccaaag                                                    20

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ccatgaactt tctgctgtct t                                                  21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
tcgatcgttc tgtatcagtc t                                                  21

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
aacacaagac caaccggaag                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gcagccattt tcagcttttc                                                    20

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
gccctggata ccaactattg c                                                  21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
```

-continued

```
tcagcacttg caggagtagc g                                          21

<210> SEQ ID NO 14
<211> LENGTH: 24
<212> TYPE: DNA
<213> ORGANISM: Artificial Sequence
<220> FEATURE:
<223> OTHER INFORMATION: Synthetic Construct

<400> SEQUENCE: 14
ccacctttca tcttcccaat tctc                                       24

<210> SEQ ID NO 15
<211> LENGTH: 18
<212> TYPE: DNA
<213> ORGANISM: Artificial Sequence
<220> FEATURE:
<223> OTHER INFORMATION: Synthetic Construct

<400> SEQUENCE: 15
gtgcggatct ggcggttg                                              18
```